United States Patent
Fabinski et al.

[11] Patent Number: 5,932,794
[45] Date of Patent: Aug. 3, 1999

[54] INSTRUMENT FOR MAGNETIC MEASUREMENT OF OXYGEN

[75] Inventors: Walter Fabinski, Kriftel; Thomas Bauer, Bad Homburg, both of Germany

[73] Assignee: Hartman & Braun GmbH & Co. KG, Frankfurt am Main, Germany

[21] Appl. No.: 09/077,059

[22] PCT Filed: Sep. 18, 1997

[86] PCT No.: PCT/DE97/02137

§ 371 Date: May 18, 1998

§ 102(e) Date: May 18, 1998

[87] PCT Pub. No.: WO98/12553

PCT Pub. Date: Mar. 26, 1998

[30] Foreign Application Priority Data

Sep. 18, 1996 [DE] Germany .......................... 196 39 989

[51] Int. Cl.⁶ .......................... G01N 31/00; G01N 27/74; G01R 33/12
[52] U.S. Cl. .......................... 73/25.02; 73/31.05; 324/204
[58] Field of Search .............. 73/31.05, 25.02; 324/204, 214

[56] References Cited

U.S. PATENT DOCUMENTS

| | | | |
|---|---|---|---|
| 2,666,893 | 1/1954 | Munday | 324/36 |
| 2,944,418 | 7/1960 | Engelhardt | 73/27 |
| 3,447,073 | 5/1969 | Gamble | 324/36 |
| 3,504,275 | 3/1970 | Eller et al. | 324/36 |
| 3,612,991 | 10/1971 | Green | 324/36 |
| 3,826,974 | 7/1974 | Kocache et al. | 324/36 |
| 3,881,152 | 4/1975 | Tasaki | 324/36 |
| 4,860,574 | 8/1989 | Maeda et al. | 73/27 A |
| 4,983,913 | 1/1991 | Krause et al. | 324/204 |
| 5,369,980 | 12/1994 | Kocache | 73/25.02 |
| 5,493,215 | 2/1996 | Otten | 324/204 |

*Primary Examiner*—Hezron Williams
*Assistant Examiner*—J. David Wiggins
*Attorney, Agent, or Firm*—Cohen, Pontani, Lieberman & Pavans

[57] ABSTRACT

The invention relates to a micro-mechanical device for determining the oxygen content in a gas mixture or gas matrix including a dumbbell-shaped element having a base plate and two volumes of the gas to be measured arranged on opposing sides of a center portion of the base plate. The center portion of the base plate is held by a clamping band which is torsionally held such that the base plate rotates about the center portion. A mirror element on the base plate is used to determine a rotational position of the base plate and a compensation coil for conducting current and creating a rotational force to counter any rotation by the base plate is arranged on the dumbell-shaped element. The dumbbell-shaped gas volumes, mirror and compensation coils are integrated as a coherent structural unit on a base plate in silicon micro-mechanical design, or the dumbbell-shaped gas volumes comprise a photo-active glass base plate and two cover plates bonded thereto and be embodied, together with the mirror and compensation coils, as a coherent structural unit.

22 Claims, 3 Drawing Sheets

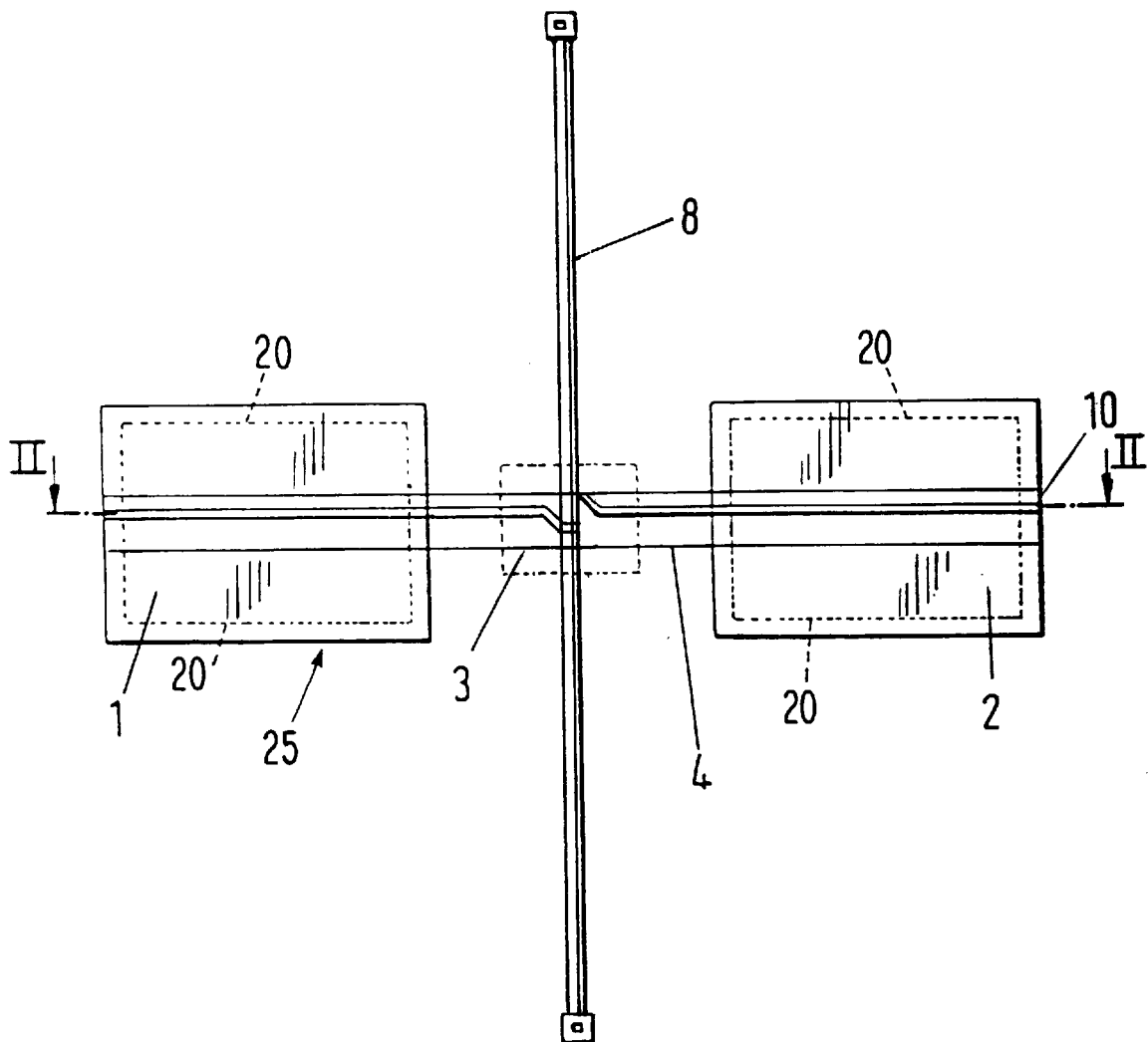
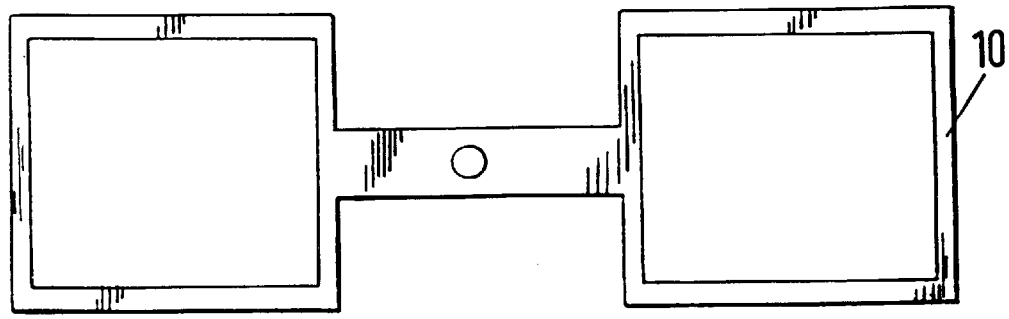

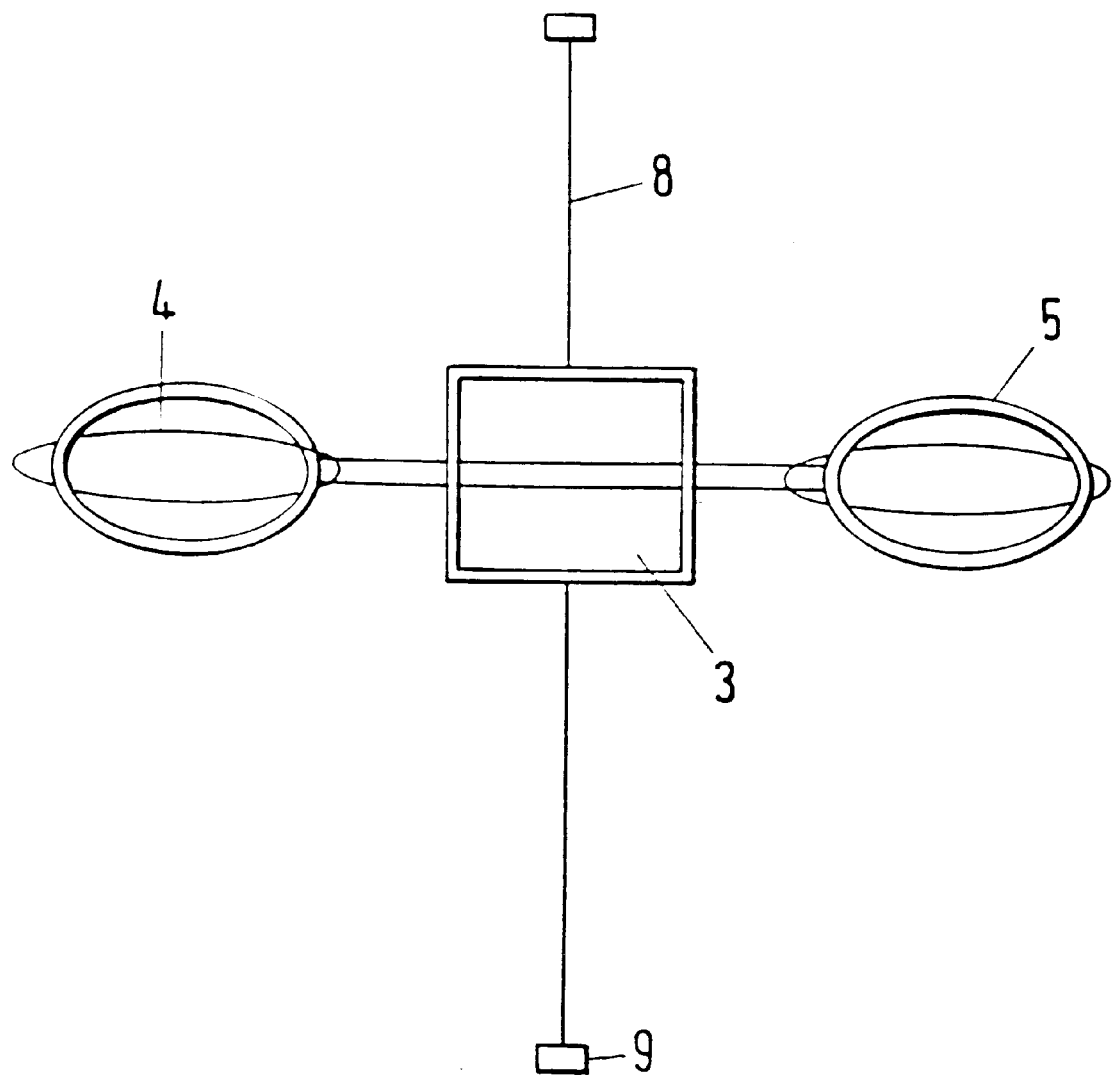

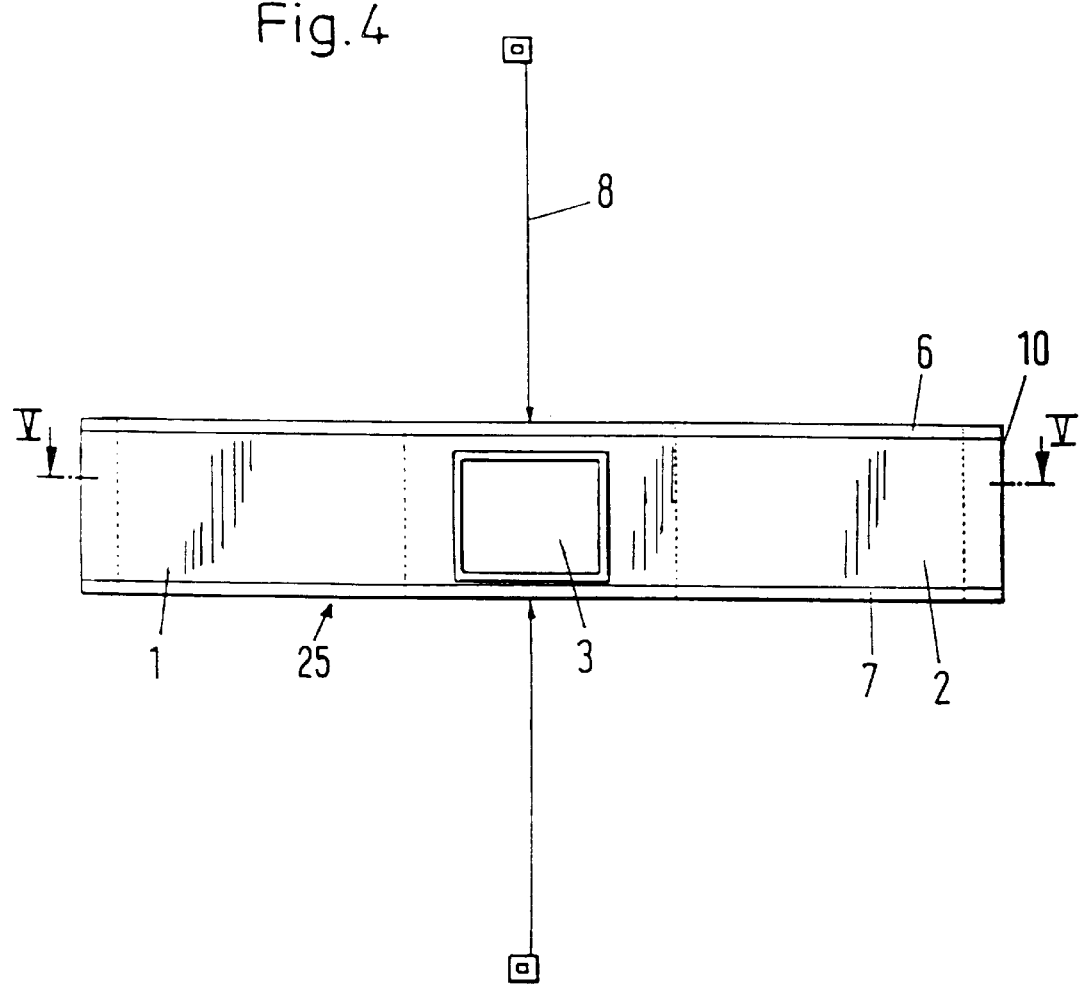
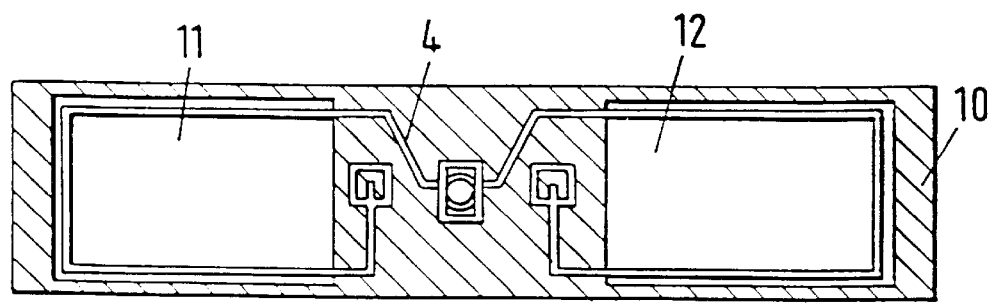

INSTRUMENT FOR MAGNETIC MEASUREMENT OF OXYGEN

BACKGROUND OF THE INVENTION

1. Field of the Invention

The invention relates to a device for determining the oxygen content of a gas mixture or gas matrix.

2. Description of the Prior Art

Oxygen and oxygen molecules have the property of being paramagnetic. This means that in an inhomogeneous magnetic field, a force is exerted on oxygen molecules. This physical effect is used in a known planner to determine oxygen content. When this is done, a directed force, proportionate to the oxygen content or quantity, is produced in the inhomogeneous magnetic field. Generally, a sensor part for measuring this effect consists of a dumbbell-shaped functional unit that can be displaced and rotated in the inhomogeneous magnetic field. As mentioned, the oxygen molecules held on both sides of the dumbbell-shaped functional unit undergo deflection in the magnetic field, resulting in a rotary displacement of the dumbbell-shaped arrangement. This rotation is compensated for by a current through a compensation coil. The position or displacement of the dumbbell is determined via a mirror, and the mirror detected position is thus proportionate to the detectable oxygen content. As noted, oxygen measurement devices of this type, which use tile magneto-mechanical method described above, have a dumbbell-shaped arrangement with corresponding gas volumes. The dumbbell, which is located within the influence of an inhomogeneous magnetic field, is rotatably suspended by a clamping band. In the presence of oxygen, the dumbbell rotates in the magnetic field to a greater or lesser extent, in a manner proportionate to the share of oxygen. By optically determining the rotational angle, it is possible, in the manner described above, to determine the share of oxygen.

Devices of this type are usually operated in compensatory operation. This means that there is a compensation coil, through which a current is run to compensate for the magnetically-mechanically produced rotation. A light beam is directed upon a mirror, which is connected to the dumbbell, and projected by reflection onto a light-sensitive sensor. The strength of the displacement is proportionate to the current and to the concentration of oxygen. The oxygen concentration can therefore be derived from amount of current needed to compensate for the rotation.

In known designs, the aforementioned components, which essentially comprise the dumbbell, magnetic elements, the rotatable functional unit and the electric compensation device, including the mirror and sensors, are produced as discrete parts and then assembled. This is an expensive method, not only because assembling the individual parts is costly, but because adjusting them to one another is, too.

SUMMARY OF THE INVENTION

The object of the invention is therefore to further develop a magnetic oxygen measurement device of the generic type in such a way that adjustment is considerably simplified.

This object is attained in a magnetic oxygen measurement device according to the invention including a dumbbell-shaped element with two glass bodies filled with a measurement gas, a clamping band for holding the center of the dumbbell-shaped element, a mirror for detecting a position of the dumbbell-shaped element and a compensation coil which receives a current to compensate for rotation of the dumbbell shaped element.

The basic principle of the invention is to structurally combine the essential parts of the arrangement using micro-mechanical techniques. According to the invention, the mirror, electrical distributors, compensation coil, corrosion protector and dumbbell-shaped element are combined in a micro-mechanical structure that can be produced in simple production steps.

In a first embodiment, the elements to be connected are, for the most part, made of silicon; in a second embodiment, glass elements are used.

The glass used has active optical properties and consists, for example, of foturan. This material is supplied in the form of glass wafers of 1–2 mm, for example, and is exposed in the contours corresponding to the recesses of the dumbbell-shaped element. The base body is worked out by means of etching processes. The recesses are bonded to a cover plate of 0.1 mm, for example, so that hermetically sealed volumes are created. A hole is provided in the center of the base body for the feed wire or clamping band.

A coil conductor is then attached to the cover plate, for example, by sputtering or evaporation physical vapor deposition (PVD). The same process is used to attach a mirror to a vertical side of the base body. The materials other than glass are made of corrosion-proof material, e.g., platinum.

The feed wires function as both the power supply line and the clamping band (mechanical holder) for the dumbbell-shaped element. They are secured by laser welding.

Advantageously, this entire structure is simpler to adjust, because many of the components that were previously assembled as discrete parts are now mechanically combined into one structural unit. As a result, it is only necessary to adjust and impose geometrical dimensions during the creation of a production matrix. Once these dimensions have been optimally established, they can be reproduced in large series with consistent accuracy. As a result, the entire arrangement becomes more economical, especially due to production steps that can be mechanized. Production errors are reduced, because it is no longer necessary for individual devices or the discrete individual parts that now have been combined to be adjusted to one another.

BRIEF DESCRIPTION OF THE DRAWINGS

In the drawings, wherein like reference characters denote similar elements:

FIG. 1 shows a first embodiment of a magnetic oxygen measurement device according to the invention constructed using a silicon micromechanical construction technique;

FIG. 2 is a top view of a dumbbell-shaped element of the magnetic oxygen measurement device along line II—II of FIG. 1;

FIG. 3 shows a prior art magnetic oxygen measurement device;

FIG. 4 shows a second embodiment of a magnetic oxygen measurement device according to the invention constructed using a glass technique; and FIG. 5 is a top view of a dumbbell-shaped element of the magnetic oxygen measurement device along line V—V of FIG. 4.

DETAILED DESCRIPTION OF THE PREFERRED EMBODIMENTS

FIG. 1 shows the embodiment according to the invention. This embodiment, like the prior art model shown in FIG. 3, has all of the components that are conventionally used. According to the invention, however, the individual components, such as gas volumes 1 and 2 arranged with a base plate 10 in a dumbbell-shaped element 25 and the other functional elements, including a mirror 3, electric connections, and a compensation coil 4, are combined in an integrated fashion into a micro-mechanical structural unit. The gas volumes 1 and 2 consist of half shells 20 produced in a silicon construction technique and connected to each other by the base plate 10. Thus, a micro-mechanical structure with closed gas volumes is created. As FIG. 2 shows, the gas volumes 1 and 2, along with the base plate 10 to which the half shells 10 are connected, are formed from a base plate 10 with eyeglass-shaped contours. The two outer areas of the base plate 10 constitute ring-shaped or eyeglass-shaped areas on which the half shells 20 are bonded, above and below. The compensation coil 4 is integrated on or in this eyeglass-shaped base plate 10. At the center of the base plate 10, namely, at the narrowed point in the middle, a surface-coated glass fiber that serves a torsion band 8 is attached. Arranged at both ends of the glass fiber are the electric connections of the compensation coil 4. Via the glass torsion band 8, the compensation coil 4 can be connected to a power source by integrated lines. This is done, for example, by providing the surface of the glass fiber with a metal or electrically conductive coating, e.g., platinum (for reasons of chemical resistance). The torsion band 8 at least the metal of electrically conductive or coating is interrupted at approximately the middle of its longitudinal extension, so that two connection paths are created for the positive and negative polarities of the compensation coil 4.

FIG. 2 shows the eyeglass-shaped base plate 10 already described in reference to FIG. 1. With the help of the base plate 10, the two opposite half shells 20 are connected by anodic bonds. The central narrowed connecting piece combines the base plate 10 and thus the half shells 20 later arranged on it into the rotatable dumbbell-shaped element 25 described above. To create the volumes 1 and 2 for the oxygen or corresponding measurement gas component, the base plate 10 is centrally arranged, as shown in FIG. 1, and on each side has an upper half shell 20 and lower half shell 20, which are bonded to the edge of the base plate 10. As already mentioned, the base plate 10 contains the integrated compensation coil 4. In the middle, i.e., where the opening is for the penetration and attachment of the torsion band 8, the surface of the connecting piece is mirrored, as FIG. 1 indicates, so that a mirror 3 is created in an integrated fashion. The mirror 3 and compensation coil 4 are applied either by deposition, sputtering or the thick-film technique. According to the invention, the aforementioned torsion strip 8 is made of a glass fiber, which is surface-coated as needed. To attain electrical conductivity as well as a chemical resistance, the surface coating may comprise of platinum. The other components car also be surface-treated, so as to attain a suitable chemical resistance for every gas mixture.

FIG. 3 shows an arrangement according to the prior art that contains all of the individual elements needed for this measurement technique. In this arrangement, the mirror 3, the connecting piece (baseplate) 10 for attaching the dumbbell-shaped glass bodies 5, the reversing wire serving as the compensation coil 4, the damping band 8 and the suspension device 9 are discrete individual elements, which must be adjusted and attached to one another. In the embodiment according to the invention in FIG. 1, the essential elements are arranged in integrated fashion on the aforementioned base plate 10 (as in FIG. 2), and thus require adjustment only during the creation of the production model.

After that, during production, further adjustment steps can be omitted, because the arrangement according to the invention are reproduced as desired.

FIG. 4 shows a further embodiment of the invention, but in a glass construction technique. The dumbbell-shaped element 25 comprises a base body 10 that, in this case, is made of glass. The selected glass is advantageously foturan. The base body 10, shown here in enlarged fashion, is actually 1 to 2 mm in size. The base body 10 is produced from a glass wafer that is exposed and etched to form with the recesses 11 and 12, which form the gas volumes arranged in a dumbbell shape. This eyeglass-shaped base body 10 is bonded to thin cover plates 6, 7 on both sides, so that two hermetically sealed gas volumes 1 and 2 are created. These are prefilled with the measurement gas component to be measured later.

A conductor forming the compensation coil 4 is then attached to one of the cover plates 6, 7 by sputtering or evaporation using, for example a physical vapor deposition (PVD method). The same process is used to apply a mirror 3 to a vertical side. The coil conductor and mirror are made of a corrosion-proof material, advantageously platinum.

The torsion strip 8 is attached to the dumbbell shaped element 25 above and below. The strip 8 thus serves for the mechanical rotary suspension of the dumbbell as well as for the contact of the compensation coil 4.

FIG. 5 shows a sectional view along Line V—V from FIG. 4. This view from above of the base body 10 with the dumbbell-shaped gas volumes 1 and 2, created by the recesses 11 and 12, also shows the course of the compensation coil 4. The coil 4 is attached to an inner side of the lower cover plate 7.

We claim:

1. An apparatus for magnetic oxygen measurement of a gas, comprising:
   a dumbbell-shaped element comprising an eyeglass-shaped base plate and two bodies filled with the gas to be measured, said base plate having a center portion connecting two ring shaped portions and each said two bodies connected at one of the two ring-shaped portions of said base plate;
   a mirror element connected on a side of said dumbbell-shaped element;
   a clamping band connected to said center portion of said dumbbell shaped element and operatively held under tension such that said base plate is rotatable about said center portion; and
   a compensation coil on said dumbbell-shaped element conducting a current, wherein said dumbbell-shaped element is positioned in a magnetic field for oxygen measurement of the gas and said compensation coil is operatively arranged for inducing a rotational force for opposing a rotation of said base plate induced by the magnetic field;
   wherein said two bodies, said mirror element, said compensation coil, and said base plate are manufactured as one integral component using silicon micromechanical construction techniques.

2. The apparatus of claim 1, wherein said clamping band comprises a glass fiber.

3. The apparatus of claim 1, wherein said clamping band comprises a metal wire.

4. The apparatus of claim 1, further comprising a n electric feed to said compensation coil comprising an electrically conductive coating on said clamping band.

5. The apparatus of claim 1, wherein each said bodies comprises a pair of half shells sealingly bonded on opposing sides of one of said two ring shaped portions.

6. The apparatus of claim 1, wherein said mirror element and said compensation coil are applied to said base plate to form said one integral component.

7. The apparatus of claim 6, wherein said mirror element and said compensation coil are deposited on said base plate by physical vapor deposition.

8. The apparatus of claim 6, wherein said mirror element and said compensation coil are deposited on said base plate by sputtering.

9. The apparatus of claim 6, wherein said mirror element and said compensation coil are deposited on said base plate by thick-film techniques.

10. The apparatus of claim 4, wherein said electrically conductive coating comprises platinum.

11. The apparatus of claim 1, wherein surfaces of said base plate and said bodies contacting the be to measured are surface-treated to react in a chemically inert fashion.

12. An micro-mechanical apparatus for magnetic oxygen measurement of a gas, comprising:

a dumbbell-shaped element comprising a base plate and photoactive glass cover plates bonded on opposing sides of said base plate, said dumbbell-shaped element further comprising two volumes filled with the gas to be measured;

a mirror element connected on a side of said dumbbell-shaped element;

a clamping band connected to a center portion of said base plate operatively held under tension such that said base plate is rotatable about said center portion of said base plate; and a compensation coil on said base plate conducting a current, wherein said dumbbell-shaped element is positioned in a in homogeneous magnetic field for oxygen measurement of the gas and said compensation coil is operatively arranged for inducing a rotational force on said base plate for opposing a rotation of said base plate as induced by the magnetic field;

wherein said mirror element, said compensation coil, said base plate and said cover plates are manufactured as one coherent structure.

13. The apparatus of claim 12, wherein said clamping band comprises a glass fiber.

14. The apparatus of claim 12, wherein said clamping band comprises a metal wire.

15. The apparatus of claim 12, further comprising an electric feed to said compensation coil comprising an electrically conductive coating on said clamping band.

16. The apparatus of claim 12, wherein each said two volumes comprises a recess in said base plate bonded on both sides to said cover plates in an occluding manner.

17. The apparatus of claim 12, wherein said mirror element is applied to said base plate and said compensation coil is applied to one of said cover plates.

18. The apparatus of claim 17, wherein said mirror element and said compensation coil are applied by physical vapor deposition.

19. The apparatus of claim 17, where in said mirror element and said compensation coil are applied by sputtering.

20. The apparatus of claim 17, wherein said mirror element and said compensation coil are applied by thick-film deposition techniques.

21. The apparatus of claim 15, wherein said electrically conductive coating comprises platinum.

22. The apparatus of claim 12, wherein surfaces of said base plate and said cover plates contacting said gas to measured are surface-treated in a chemically inert fashion.

* * * * *